(12) United States Patent
Walters et al.

(10) Patent No.: US 11,350,919 B2
(45) Date of Patent: Jun. 7, 2022

(54) PUNCTURE LOCATING SYSTEM WITH BLOOD PULSATION INDICATOR

(71) Applicant: Teleflex Life Sciences Limited, Valletta (MT)

(72) Inventors: Greg A. Walters, Exton, PA (US); Shawn Sabu Cherian, Poughquag, NY (US); Joseph Todd Grintz, Glenmoore, PA (US)

(73) Assignee: Teleflex Life Sciences Limited, Valletta (MT)

( * ) Notice: Subject to any disclaimer, the term of this patent is extended or adjusted under 35 U.S.C. 154(b) by 188 days.

(21) Appl. No.: 16/279,577

(22) Filed: Feb. 19, 2019

(65) Prior Publication Data

US 2020/0261068 A1 Aug. 20, 2020

(51) Int. Cl.
| | | |
|---|---|---|
| *A61B 17/00* | (2006.01) | |
| *A61B 5/026* | (2006.01) | |
| *A61B 5/00* | (2006.01) | |
| *A61B 5/0215* | (2006.01) | |
| *A61M 29/00* | (2006.01) | |
| *A61M 25/06* | (2006.01) | |
| *A61B 90/00* | (2016.01) | |

(52) U.S. Cl.
CPC .......... *A61B 17/0057* (2013.01); *A61B 5/026* (2013.01); *A61B 5/489* (2013.01); *A61B 5/0215* (2013.01); *A61B 2017/00672* (2013.01); *A61B 2090/062* (2016.02); *A61B 2090/0807* (2016.02); *A61M 25/0693* (2013.01); *A61M 29/00* (2013.01)

(58) Field of Classification Search
CPC ..... A61B 17/0057; A61B 5/026; A61B 5/489; A61B 2090/062; A61B 2090/0807; A61B 5/0215; A61B 2017/00672; A61B 2017/00623; A61M 25/0693; A61M 29/00; A61M 2025/0008; A61M 2025/0681
See application file for complete search history.

(56) References Cited

U.S. PATENT DOCUMENTS

| | | | |
|---|---|---|---|
| 4,064,550 | A | 12/1977 | Dias et al. |
| 4,760,847 | A | 8/1988 | Vaillancourt |
| 5,021,059 | A | 6/1991 | Kensey et al. |

(Continued)

FOREIGN PATENT DOCUMENTS

| | | |
|---|---|---|
| EP | 0664687 B2 | 8/2003 |
| EP | 1307141 B1 | 10/2007 |
| EP | 3093038 B2 | 5/2019 |

OTHER PUBLICATIONS

Nash, et al. "The Angio-Seal Hemostatic Puncture Closure Device, Concept and Experimental Results," Herz Urban & Vogel, 1999, pp. 597-606, Kensey Nash Corporation, Exton, Pennsylvania, USA.

(Continued)

*Primary Examiner* — Kathleen S Holwerda
*Assistant Examiner* — Uyen N Vo
(74) *Attorney, Agent, or Firm* — Gregory A. Grissett; Joseph P. Mathew

(57) ABSTRACT

Disclosed are puncture sealing systems and methods of locating a puncture site within a vessel. The systems can include elongated dilators and access sheaths that are configured to locate the puncture site within a vessel so that the position of the puncture site relative to a distal end of the access sheath is known during a puncture sealing procedure.

17 Claims, 9 Drawing Sheets

(56) References Cited

U.S. PATENT DOCUMENTS

| | | | |
|---|---|---|---|
| 5,108,375 A | 4/1992 | Harrison et al. | |
| 5,193,106 A | 3/1993 | DeSena | |
| 5,282,827 A | 2/1994 | Kensey et al. | |
| 5,292,309 A | 3/1994 | Tassel et al. | |
| 5,306,254 A | 4/1994 | Nash et al. | |
| 5,324,306 A | 6/1994 | Makower et al. | |
| 5,356,386 A | 10/1994 | Goldberg et al. | |
| 5,441,517 A | 8/1995 | Kensey et al. | |
| 5,469,847 A | 11/1995 | Zinreich et al. | |
| 5,514,112 A * | 5/1996 | Chu | A61M 27/00 604/265 |
| 5,755,746 A | 5/1998 | Lifshey et al. | |
| 5,980,492 A | 11/1999 | Rosen et al. | |
| 5,984,895 A | 11/1999 | Padilla et al. | |
| 6,090,130 A | 7/2000 | Nash et al. | |
| 6,193,670 B1 | 2/2001 | Tassel et al. | |
| 6,425,911 B1 | 7/2002 | Akerfeldt et al. | |
| 6,494,848 B1 | 12/2002 | Sommercorn et al. | |
| 6,682,489 B2 | 1/2004 | Tenerz et al. | |
| 7,025,748 B2 | 4/2006 | Ashby | |
| 7,044,916 B2 | 5/2006 | Tenerz et al. | |
| 7,073,509 B2 | 7/2006 | Tenerz et al. | |
| 7,285,097 B2 | 10/2007 | Tenerz et al. | |
| 7,618,370 B2 | 11/2009 | Choi et al. | |
| 7,648,493 B2 | 1/2010 | Forsberg et al. | |
| 7,753,935 B2 | 7/2010 | Brett et al. | |
| 7,850,654 B2 | 12/2010 | Belhe et al. | |
| 8,273,094 B2 | 9/2012 | Belhe et al. | |
| 8,382,793 B2 | 2/2013 | Egnelöv et al. | |
| 8,401,620 B2 | 3/2013 | Velusamy et al. | |
| 8,632,470 B2 | 1/2014 | Stahmann et al. | |
| 9,421,349 B2 | 8/2016 | Miller | |
| 9,554,785 B2 | 1/2017 | Walters et al. | |
| 9,592,039 B2 | 3/2017 | Glazier et al. | |
| 10,039,606 B2 | 8/2018 | Blau et al. | |
| 10,182,804 B2 | 1/2019 | Walters et al. | |
| 10,835,225 B2 | 11/2020 | Walters et al. | |
| 2001/0044639 A1 | 11/2001 | Levinson | |
| 2004/0147846 A1 | 7/2004 | Mueller et al. | |
| 2004/0243007 A1 | 12/2004 | Tenerz et al. | |
| 2005/0085854 A1 * | 4/2005 | Ginn | A61B 17/0057 606/213 |
| 2005/0107750 A1 | 5/2005 | Barongan | |
| 2005/0107820 A1 | 5/2005 | Forsberg et al. | |
| 2006/0282106 A1 | 12/2006 | Cole et al. | |
| 2007/0123936 A1 | 5/2007 | Goldin et al. | |
| 2008/0097218 A1 | 4/2008 | Vrba | |
| 2008/0306509 A1 | 12/2008 | Osborne | |
| 2008/0319475 A1 | 12/2008 | Clark et al. | |
| 2009/0082784 A1 | 3/2009 | Meissner et al. | |
| 2009/0156929 A1 | 6/2009 | Franco | |
| 2011/0054456 A1 | 3/2011 | Thompson et al. | |
| 2011/0172767 A1 | 7/2011 | Rathi et al. | |
| 2011/0224721 A1 | 9/2011 | Edwards et al. | |
| 2012/0203328 A1 | 8/2012 | Yribarren | |
| 2012/0283770 A1 | 11/2012 | Kramer et al. | |
| 2012/0296275 A1 | 11/2012 | Martin et al. | |
| 2013/0245644 A1 | 9/2013 | Tegels | |
| 2014/0051994 A1 | 2/2014 | Graumann et al. | |
| 2014/0180332 A1 * | 6/2014 | Walters | A61M 25/09 606/213 |
| 2015/0313582 A1 * | 11/2015 | Phillips | A61B 17/0057 606/214 |
| 2015/0367103 A1 * | 12/2015 | Pajunk | A61M 25/0043 604/512 |
| 2017/0100113 A1 | 4/2017 | Walters et al. | |
| 2017/0291016 A1 | 10/2017 | Fumiyama | |
| 2019/0142404 A1 | 5/2019 | Walters et al. | |
| 2021/0045724 A1 | 2/2021 | Walters et al. | |

OTHER PUBLICATIONS

PCT International Search Report and Written Opinion dated Jun. 5, 2020, in application PCT/US2020/016492 filed Feb. 4, 2020.

St. Jude Medical, "Angio-Seal Vascular Closure Device Millennium Platform," Brochure, 2001, 10 pp.

* cited by examiner

PUNCTURE LOCATING SYSTEM WITH BLOOD PULSATION INDICATOR

TECHNICAL FIELD

The present application relates to a puncture locating system and method, and in particular, to a puncture location system utilizing a flexible member to indicate blood pulsations.

BACKGROUND

During the use of vascular closure systems after vascular interventions, it is often important to know the location of a puncture in the vessel, and in particular, providing for exact placement of vascular sheaths. Typically, a "blood flashback" method is used to position a vascular device.

SUMMARY

An embodiment of the present disclosure includes a puncture locating device for locating a puncture in a blood vessel. The puncture locating device includes an elongated dilator having a distal end, a proximal end that is opposite the distal end, an outer surface, an internal channel that extends from the distal end to the proximal end, an inlet opening that is open to the internal channel and is spaced from the distal end, and an outlet opening disposed between the proximal end and the inlet opening. The dilator also includes a flexible barrier attached to the elongated dilator and overlying the outlet opening so that the flexible barrier and the outer surface proximate the outlet opening at least partially define an internal volume. When the elongated dilator is inserted into the puncture of the blood vessel, blood flows into the inlet opening through the channel and out the outlet opening into the internal volume, such that, pulsations in the blood flow cause the flexible barrier to pulse, thereby generating a visual and tactile indication of presence of the inlet opening in the blood vessel.

Another embodiment of the present disclosure includes a puncture locating device for locating a puncture in a blood vessel. The puncture locating device includes an elongated dilator having a distal end, a proximal end that is opposite the distal end, an outer surface, an internal channel that extends from the distal end to the proximal end, an inlet opening that is open to the internal channel and is spaced from the distal end, an outlet opening disposed between the proximal end and the inlet opening. The puncture locating device includes a blood pulsation indicator overlying the outlet opening so that the blood pulsation indicator and the outer surface proximate the outlet opening at least partially define an internal volume. When the elongated dilator is inserted into the puncture of the blood vessel, blood flows into the inlet opening through the outlet opening into the internal volume, such that, pulsations in the blood flow cause the blood pulsation indicator to pulse, thereby generating a visual and tactile indication of presence of the inlet opening in the blood vessel.

An embodiment of the present disclosure includes a method for locating a puncture in a blood vessel of a patient. The method includes inserting a guidewire through the puncture into the vessel so that a distal end of the guidewire is inside the vessel and the guidewire extends out of the puncture. The method also includes inserting a proximal end of the guidewire into a distal end of a dilator, the dilator including a proximal end spaced from the distal end, and a plurality of markings along an outer surface of the dilator. The method also includes moving the dilator along the guidewire in a distal direction until blood in the blood vessel flows through an inlet opening of the dilator and into an internal volume at least partially defined by the outer surface of the dilator and a flexible barrier attached to the dilator, whereby the flexible barrier repeatedly pulses in response to pressure pulsations of blood in the blood vessel. The method also includes retracting the dilator in a proximal direction along the guidewire until the flexible barrier no longer pulses. The method also includes noting a marking of the plurality of markings on the dilator that is adjacent to the surface of the patient's skin when flexible barrier no longer pulses. This, in turn, provides an indication of a depth at which the puncture is present.

BRIEF DESCRIPTION OF THE DRAWINGS

The foregoing summary, as well as the following detailed description of example embodiments of the application, will be better understood when read in conjunction with the appended drawings, in which there is shown in the drawings example embodiments for the purposes of illustration. It should be understood, however, that the application is not limited to the precise systems and methods shown. In the drawings:

FIG. 5 is a cross-sectional view of the elongated dilator take along line 5-5 in

FIG. 2;

DETAILED DESCRIPTION OF ILLUSTRATIVE EMBODIMENTS

Figure 1:
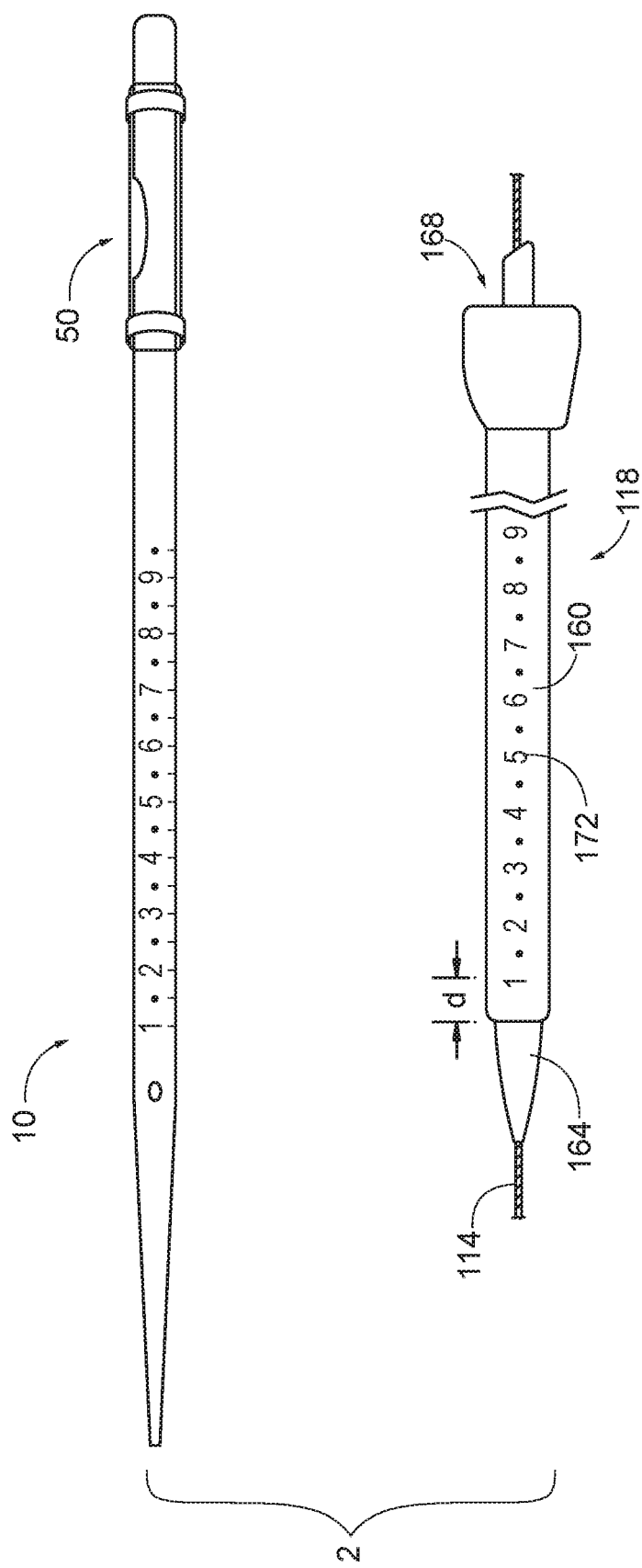
FIG. 1 is a top plan view of a puncture location system including a elongated dilator and an access sheath according to an embodiment of the present disclosure.
Figure 2:
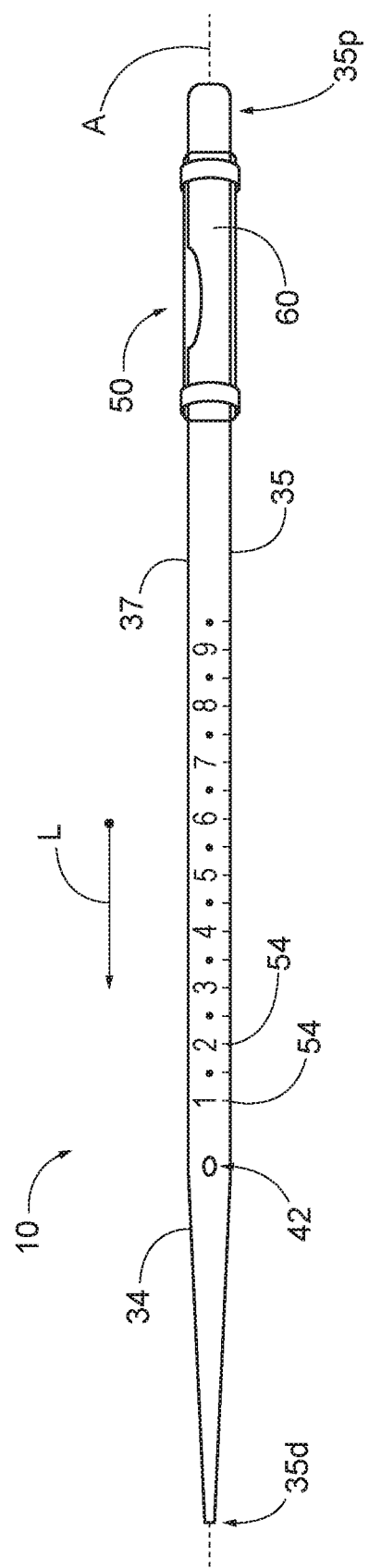
FIG. 2 is a top plan view of the elongated dilator shown in FIG. 1.

Certain terminology is used in the following description for convenience only and is not limiting. The words "right", "left", "lower" and "upper" designate directions in the drawings to which reference is made. The words "proximally" and "distally" refer to directions toward and away from, respectively, the individual operating the system. The terminology includes the above-listed words, derivatives thereof and words of similar import.

Referring to FIG. 1, a puncture locating system 2 includes an elongated dilator 10 and an access sheath 118 used in locating a puncture in a vessel during or along with an interventional cardiovascular procedure. Typically, before an interventional cardiovascular procedure, a puncture may be made in the femoral artery. In one example, a vascular closure device composed of an absorbable anchor, a folding sealing plug, a suture and a downward locking member have been developed and may be used to seal these punctures. However, before sealing can occur the depth at which the device needs to be inserted must be attained. Currently, the procedure is conducted with a puncture locator comprising of two inlet holes towards the distal end and one outlet opening at the proximal end. Conventional puncture locators allow blood to flow through the dilator and out an outlet opening when the inlet hole is present within the circulatory tract. The present disclosure, however, includes embodiments of puncture location system comprising an elongated dilator 10 with a blood pulsation indicator 50, as will be further explained below.

Figure 5:
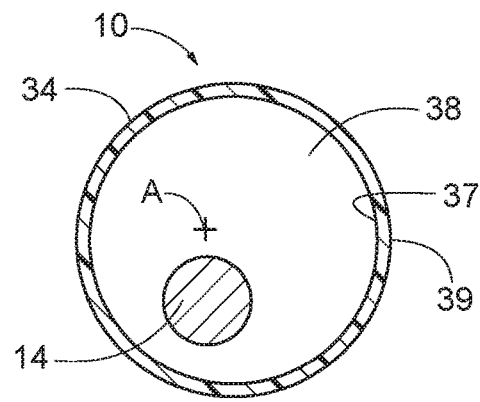

Referring to FIGS. 2-5, the elongated dilator 10 is configured to locate a puncture site 12 (FIGS. 7-9) in a vessel 13 with the blood pulsation indicator 50. The elongated dilator 10 includes a dilator body 34 that is elongated along a central longitudinal axis A in a first direction L. The first direction may be referred to as a longitudinal direction in this disclosure. The dilator body 34 defines a proximal end 35p and a distal end 35d that is spaced from the proximal end 35p along the first direction L. The distal end 35d of the dilator may be tapered to facilitate entry into the vessel. The dilator body further defines an inner surface 37, which may define an internal guide channel 38, and an outer surface 39 (FIG. 5). The elongated dilator 10 is configured to be moved along a guidewire 14 toward the puncture site 12 such that the elongated dilator 10 enters the vessel 13 through the puncture site 12. As the elongated dilator 10 enters the vessel 13 the elongated dilator 10 dilates the puncture site 12.

The elongated dilator is sized for a range of procedures. In one embodiment, the outer surface 39 defines an outer cross-sectional dimension that is substantially perpendicular to the central longitudinal axis A and the outer cross-sectional dimension is at least about 2.50 mm. In one example, the outer cross-sectional dimension is at least about 2.50-5.0 mm. However, dimensions outside of this range are possible.

Referring to FIG. 5, the internal guide channel 38 that extends through the dilator body 34 along the first direction L from the distal end 35d through to the proximal end 35p. The internal guide channel 38 is configured to receive the guidewire 14 such that the elongated dilator 10 can be moved along the guidewire 14 toward the puncture site 12. The internal guide channel 38 at the distal end 35d and proximal end 35p can have a diameter that is substantially equal to that of the guidewire 14 so that the elongated dilator 10 can move along the guidewire 14 in a controlled manner.

Referring to FIGS. 2-5, the dilator 10 can further define a blood inlet hole 42 and a blood outlet opening 46. The blood inlet hole 42 that extends through the dilator body 34 along a direction that is transverse to the first direction L. The blood outlet opening 46 that extends through the dilator body 34 proximal to the blood inlet hole 42. The blood inlet hole 42 and the blood outlet opening 46 are in fluid communication with each other such that when the blood inlet hole 42 enters the vessel 13, blood from the vessel 13 will enter the blood inlet hole 42 and exit the blood outlet opening 46 into the blood pulsation indicator 50, to thereby indicate that the blood inlet hole 42 has entered the vessel 13, as further explained below. In the illustrated embodiment, the blood inlet and outlet openings 42 and 46 extend into the guide channel 38 such that blood entering the blood inlet hole 42 will travel through the guide channel 38, around the guidewire 14, and out the blood outlet opening 46 into the blood pulsation indicator 50. It should be appreciated, however, that in some embodiments, the guide channel 38 and the channel through which the blood flows can be separate and distinct from each other, as desired. In particular, the guide channel 38 is sized to have a tight fit around the guidewire.

As shown in FIGS. 2-5, the blood pulsation indicator 50 is used to locate the puncture. More specifically, the blood pulsation indicator 50 is configured to be responsive to presence of pulsatile blood flow inside the dilator 10 when the inlet hole is located inside the vessel. As shown, the blood pulsation indicator 50 includes a flexible barrier 60 attached to the elongated dilator 10 and overlying the outlet opening 46. Configured this way, the flexible barrier 60 and the outer surface 39 proximate the outlet opening 46 at least partially defines an internal volume IV. When the elongated dilator 10 is inserted into the puncture 12 of the blood vessel 13, blood flows into the inlet opening 42 through the outlet opening 46 into the internal volume IV such that, pulsations in the blood flow cause the flexible barrier 60 to pulse, thereby generating a visual and tactile indication of presence of the inlet opening 42 in the blood vessel 13.

The flexible barrier 60 may be formed from a polymeric material that is flexible, yet durable enough to withstand pulsatile flow. For example, the flexible barrier may be polyvinylchloride, polyethylene, polyurethane, polyamides, and/or copolymer thereof. The flexible barrier can be planar shape, a sleeve, or form part of pocket, pouch, bag or other structure that can enclose a fluid.

Figure 3:
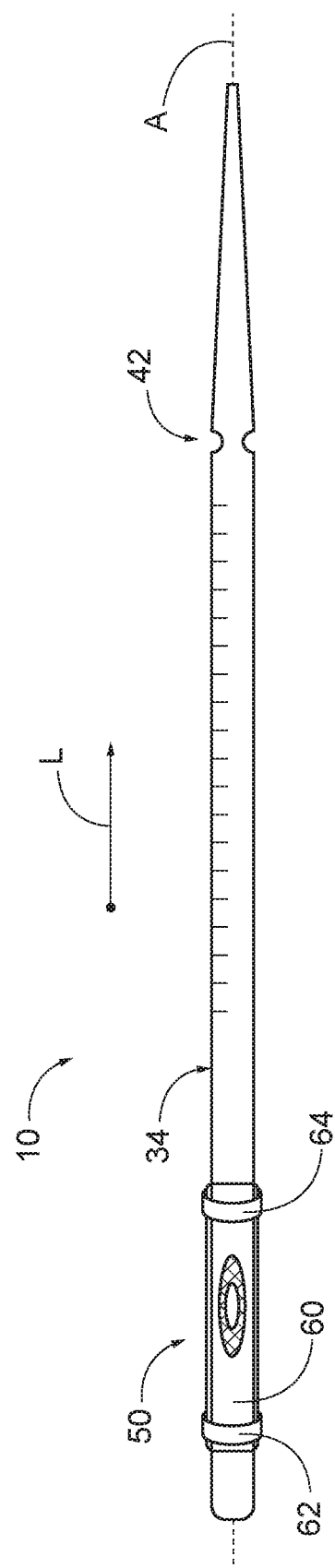
FIG. 3 is a side view of the elongated dilator shown in FIG. 2.
Figure 4:
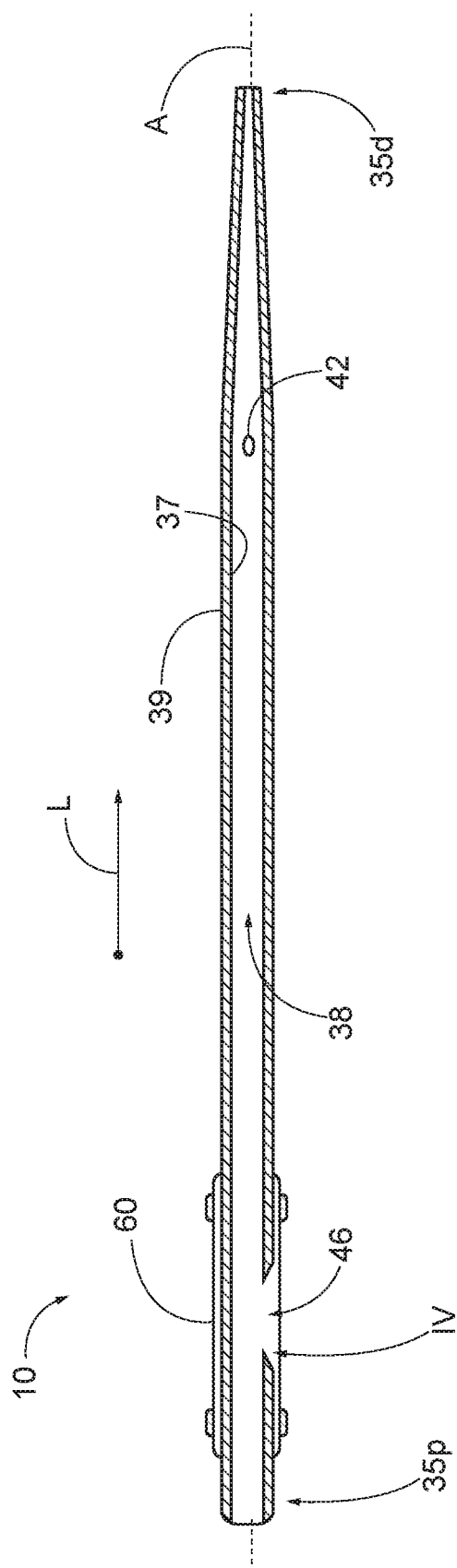
FIG. 4 is a cross-sectional view of the locating dilator taken along line 3-3 in FIG. 2.

The flexible barrier 60 may overlie the outlet opening to form an internal volume. In the illustrated embodiment, as shown in FIG. 3, attachment members 62 and 64 secure the flexible barrier in place on the dilator body 34. In one example, the flexible barrier may only overlie a portion of the dilator body 34. In other configurations, the flexible barrier may be in form of a sleeve that surrounds an entirety of the dilator body 34 proximate the outlet opening 46.

The blood pulsation indicator 50 may have configurations other than what is specifically illustrated. For example, in one alternative embodiment, the flexible barrier may be part of a flexible container that is attached to the elongated dilator. For instance, the flexible container may be flexible bag or bladder attached to the dilator.

In addition, the dilator may further comprise a handle member disposed on the elongated dilator. In such an embodiment, the elongated dilator includes a port disposed in the outlet opening 46. The flexible barrier is attached to the handle member such that the port extends from the elongated dilator to the flexible barrier.

Now, in reference to FIGS. 2-5, the elongated dilator 10 can further include a plurality of depth markings 54 spaced from each other along the first direction L between the inlet opening 42 and outlet opening 46. The depth markings 54 can be used to visually note the depth or otherwise the location of the puncture site 12 of the vessel 13 when the elongated dilator 10 has been positioned within the vessel. In the illustrated embodiment, the depth markings 54 are numbers on the dilator body 34. It should be appreciated, however, that the depth markings 54 can have other configurations as desired. For example, the depth markings can be configured as symbols as desired. The depth markings 54 can be used to locate the puncture site 12. That is, after a position of the puncture site 12 has been located with the blood inlet hole 42, a position of a first visible marking of the plurality of depth markings 54 on the dilator that is adjacent the patient's skin can be noted when the blood flows. Therefore, the position of the puncture site 12 can be known for the remainder of the procedure. The noted first marking can be noted with a sticker that is placed directly on the patient's skin as desired. It should be appreciated, however, that the first depth marking can be noted using other configurations as desired. For example, the first depth marking can be noted with a tag, card, clip, etc. In an alternative embodiment, the depth markings of this embodiment can either be used alone or in combination with the radiopaque markers.

The puncture sealing system 2 can further include an access sheath 118 that is also configured to be moved along the guidewire 14 toward the puncture site 12 and into the vessel 13 so as to further dilate the puncture site 12 and subsequently provide access to the vessel 13. The access sheath 118 can then receive a vascular sealing device 190 that is configured to seal the puncture site 12. It should be appreciated, however, that the system can include additional dilators that have cross-sectional diameters that are different (e.g. greater) than the diameter of the locating dilator 10 but less than that of the access sheath 118 so that the puncture site 12 can be gradually dilated and prepared for the access sheath 118. Both the locating dilator 10 and the access sheath 118 include respective depth markings that are configured to aid in locating the puncture site 12, as will be further described below.

Figure 6:
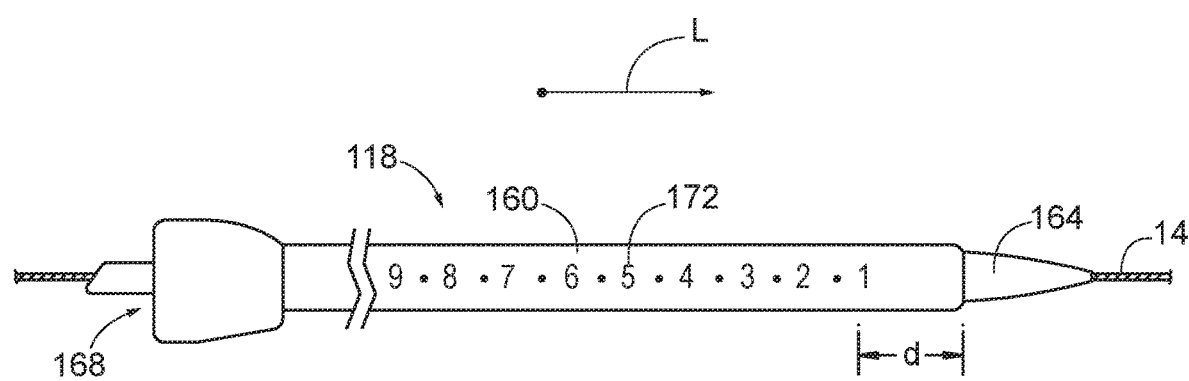
FIG. 6 is a top plan view of the access sheath of the puncture sealing system shown in FIG. 1.

Now referring to FIG. 6, the access sheath 118 includes a sheath body 160 that is elongate along the first direction L and a sheath dilator 164 that is coupled within an access channel 168 of the sheath body 160. The access channel 168 extends through the sheath body 160 from a proximal end through to a distal end of the sheath body 160 and is configured to provide an access path to the puncture site 12 after the sheath dilator 164 has been removed from the access channel 168. The access sheath 118, like the elongated dilator 10, is configured to be moved along the guidewire 14 toward the puncture site 12 such that the distal end of the access sheath 118 enters the vessel 13.

With continued reference to FIG. 6, the access sheath 118 further includes a plurality of depth markings 172 spaced from each other along the first direction L on the sheath body 160. The depth markings 172 correspond to the depth markings 54 on the elongated dilator 10 such that as the access sheath 118 is inserted into the vessel 13 the location of the distal end of the access sheath 118 relative to the puncture site 12 can be known because of the depth markings 172. In the illustrated embodiment, the depth markings 172 are numbers. It should be appreciated, however, that the depth markings 172 can have other configurations as desired so long as they somehow correspond to the depth markings 54. The depth markings 172 can be used to position the sheath body 160 so that a closure device 190 that is to be moved into the access channel 168 will be properly positioned for sealing of the puncture site 12. For example, the sheath body 160 can be positioned such that a first marking of the depth markings 172 that corresponds to the noted first visible marking on the dilator 10 is the first visible marking on the access sheath 118. When the first visible marking of the access sheath 118 corresponds to the noted first visible marking on the elongated dilator 10, the appropriate amount of sheath body 160 will be disposed within the vessel 13. It should be appreciated, however, that in some embodiments, the depth markings 172 can be placed on the closure device 190 rather than the sheath body 160.

As shown in FIG. 6, a distance d between a distal end of the access sheath 118 and a first marking of the plurality of depth markings 172 may generally correspond to the distance between the distal end of the puncture dilator and its first marking of the plurality of markings.

Figure 7:
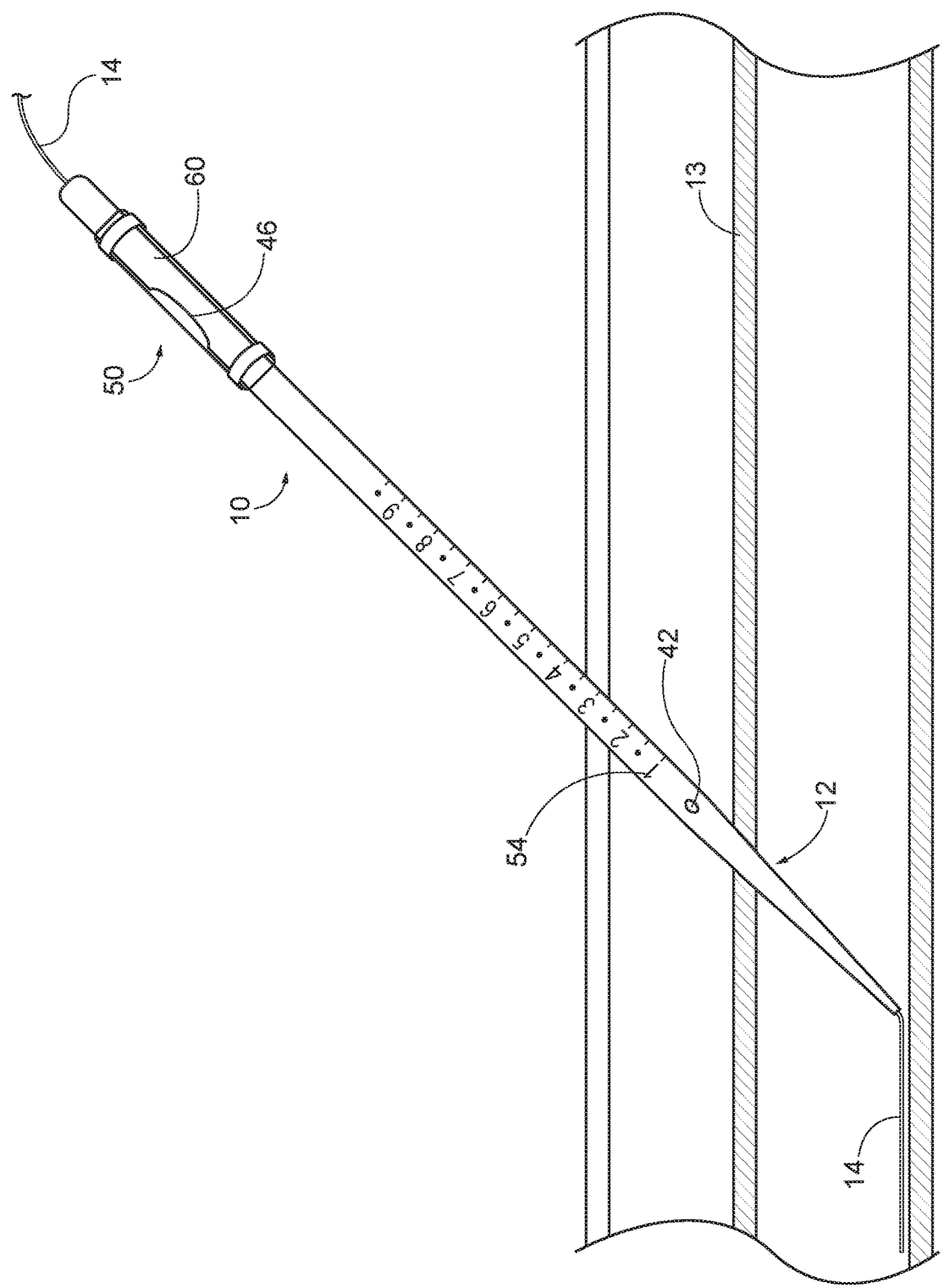
FIG. 7 is a schematic showing the elongated dilator of FIG. 1 positioned so the distal end of the dilator is disposed within a vessel and a blood intel hole is outside the vessel.
Figure 8:
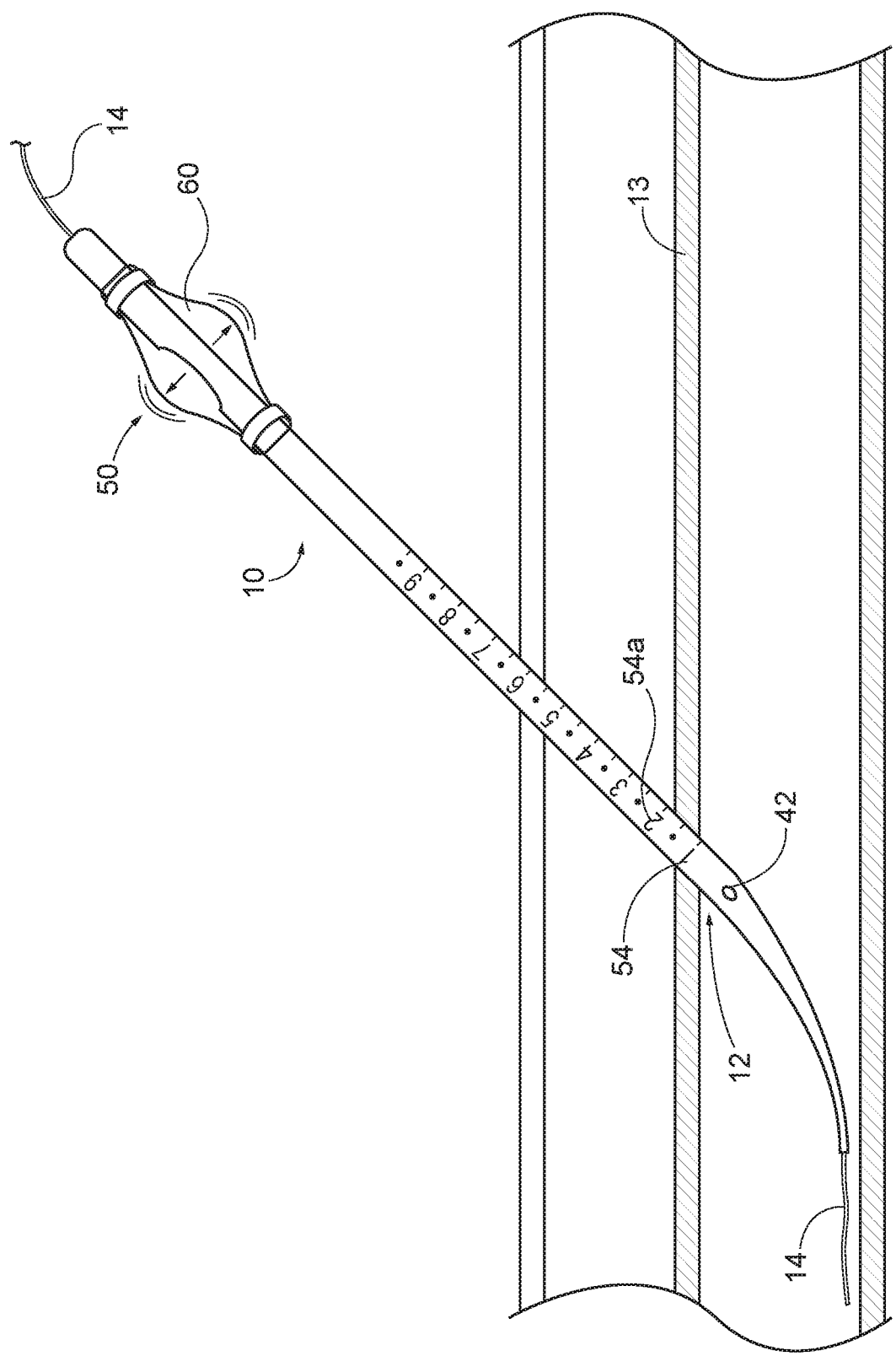
FIG. 8 is a schematic showing the elongated dilator of FIG. 1 positioned such that the inlet hole is disposed within a vessel proximate to a vessel puncture and blood pressure in the vessel causing the puncture indicator to pulsate.
Figure 9:
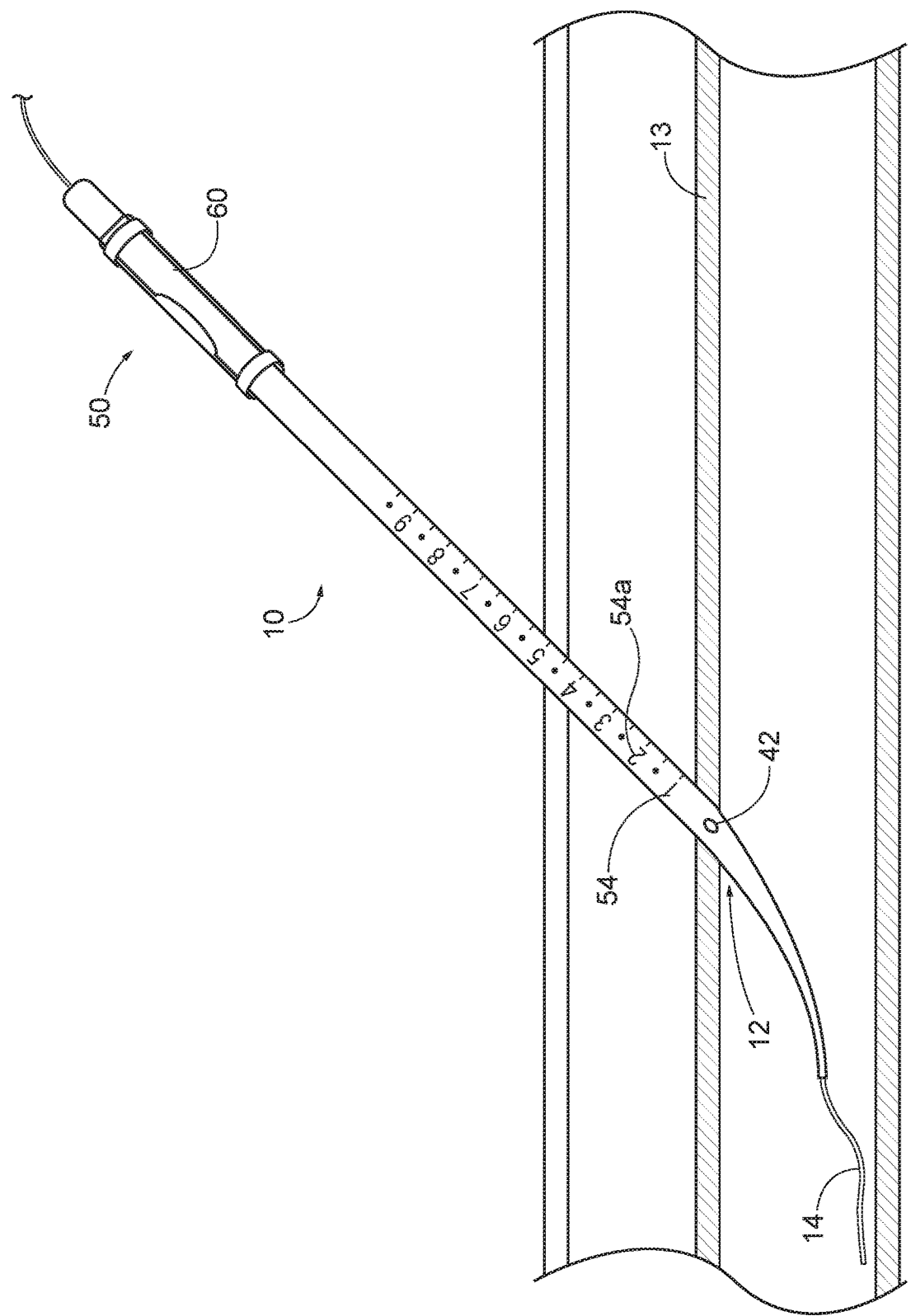
FIG. 9 is a schematic showing the elongated dilator of FIG. 1 retracted from the position shown in FIG. 8 such that the inlet hole is located at the vessel puncture.

Now referring to FIGS. 7-9, the guide wire 14 can be inserted through the puncture site 12 and into the vessel 13 such that a portion of the guidewire 14 protrudes from the vessel. Once the guidewire 14 is positioned, a proximal end of the guidewire 14 can be inserted into the distal end of the elongated dilator 10. As shown in FIG. 8, the elongated dilator 10 can then be moved along the guidewire 14 until the distal end of the elongated dilator 10 and the blood inlet hole 42 enter the vessel 13 such that blood flows into the inlet hole 42 and into the blood pulsation indicator 50, causing the flexible barrier 60 to pulsate, thereby indicating the inlet hole 42 is inside the vessel tract. In this scenario the blood within the patient will have a new avenue available to flow within, once the blood begins to flow through the inlet opening 42 and out the outlet opening 46 it will be caught within a flexible barrier 60. Once the dilator 10 has been inserted into the circulatory track the flexible barrier 60 will begin to mimic the flow rate and pressure inherent within the vessel. This will cause the flexible barrier 60 to pulsate and will supply the practitioner with both a visual and tactile indicator for when the dilator 10 is within the vessel. From there a slow removal of the dilator 10 is performed, from this action the depth of the puncture can be ascertained, which is when the pulsation of the flexible barrier 60 ceases. Once the pulsations have ceased the depth can be collected according to the depth marking visible just above skin level of the patient. In other words, the position of the puncture site 12 can be confirmed via feedback of blood flow entering the blood pulsation indicator 50 by alternatingly inserting and retracting the elongated dilator 10. As shown in FIG. 7, after the position of the puncture site 12 has been located, a first visible marking 54a of the dilator 10 can be noted. That is a first visible marking 54a that is adjacent the patient's skin can be noted. It should be appreciated, that in some embodiments, the elongated dilator 10 can be positioned over the guidewire 14 prior to the guidewire being inserted into the vessel 13.

Figure 10:
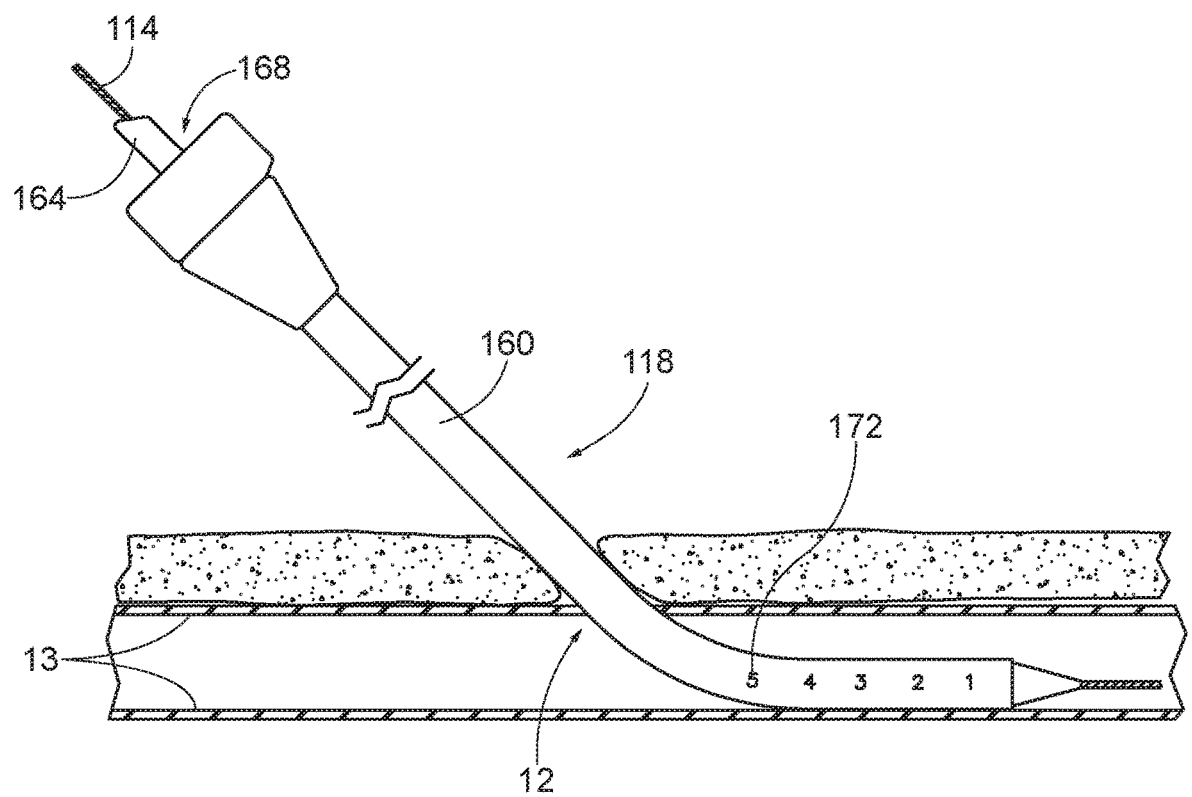
FIG. 10 is a schematic showing the access sheath of FIG. 1 being moved into the vessel along the guidewire.
Figure 11:
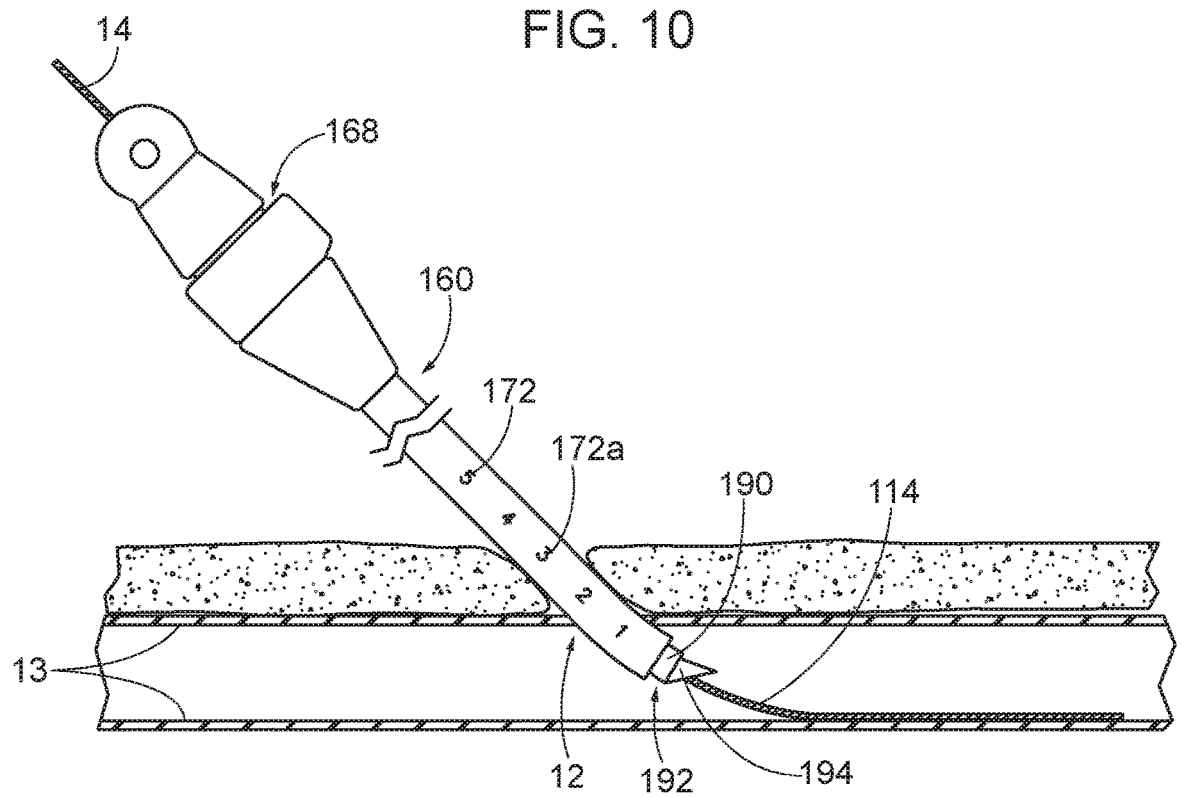
FIG. 11 is a schematic showing the access sheath removed from the access channel and the sheath body positioned such that a depth marking on the sheath body that corresponds to the at least one marking on the elongated dilator is visible above the surface of the skin.

As shown in FIG. 10, after the elongated dilator 10 has been removed from the guidewire 14 and any subsequent dilators have been removed, the access sheath 118 can be moved along the guidewire 14 toward the puncture site 12 such that the distal end of the access sheath 118 enters the vessel 13 through the puncture site 12. In particular, the proximal end of the guidewire 14 is inserted into the distal end of the sheath dilator 164. And then the sheath body 160 and sheath dilator 164 can be moved together along the guidewire 14 toward the puncture site 12. Once inserted, the sheath dilator 164 can be pulled proximally such that the sheath dilator 164 is removed from the access channel 168.

After the sheath dilator 164 has been removed, a vascular closure procedure can be performed through the access channel 168. Therefore, a closure device 190 can be moved into the access channel 168 until a distal portion 192 (e.g. at least a portion of a toggle 194) of the closure device 190 is distal to the distal end of the sheath body 160. As shown in FIG. 5C the access sheath 118 can then be moved such that a first visible marking 172a of the sheath body 160 that is visible adjacent the patient's skin corresponds with the noted first visible marking 54a of the elongated dilator 10. It should be appreciated, that the closure device 190 can be moved into the access channel 168 either prior to or after the positioning of the access sheath 118 such that the first visible marking 172 corresponds to the noted depth marking 54. When the access sheath 118 is properly positioned, the closure device 190 will be positioned such that the sealing procedure can be completed. It should be appreciated, that while in the illustrated embodiment, in some embodiment's the depth markings 172 are on the sheath body 160, the depth markings can be on the closure device 190, as desired. Furthermore, it should be appreciated, that in such embodiments, the access sheath 118 can be pulled completely out of the vessel 13 when the closure device 190 is properly positioned.

While the foregoing description and drawings represent the preferred embodiment of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one component may be used and/or interchanged with features described in another component. The presently disclosed embodiment is therefore to be considered in all respects as illustrative and not restrictive, the scope of the invention being indicated by the appended claims, and not limited to the foregoing description.

It should also be noted that the use of the present invention may occur at different points of the surgical procedure then specified previously. For instance, rather than being utilized before the introduction of the closure device it may instead be used to ascertain the depth of the initial incision prior to the surgical procedure being fully performed.

What is claimed is:

1. A puncture locating device for locating a puncture in a blood vessel, the puncture locating device comprising:
    an elongated dilator having a distal end, a proximal end that is opposite the distal end along a central axis, an outer surface, an internal channel that extends from the distal end to the proximal end along the central axis, an inlet opening that is open to the internal channel and is spaced from the distal end, and an outlet opening disposed between the proximal end and the inlet opening;
    a flexible barrier attached to the elongated dilator and overlying the outlet opening so that the flexible barrier and the outer surface proximate the outlet opening at least partially define an internal volume, wherein the flexible barrier is movably responsive to pressure pulsations outwardly from the central axis of the elongated dilator; and
    wherein when the elongated dilator is inserted into the puncture of the blood vessel, blood flows into the inlet opening through the outlet opening into the internal volume, such that, pulsations in the blood flow cause the flexible barrier to pulse outwardly, thereby generating a visual and tactile indication of presence of the inlet opening in the blood vessel.

2. The puncture locating device of claim 1, wherein the flexible barrier is a polymeric material.

3. The puncture locating device of claim 1, wherein the elongated dilator includes a plurality of markings disposed along the outer surface between the inlet opening and the outlet opening.

4. The puncture locating device of claim 1, wherein the distal end of the elongated dilator is tapered.

5. The puncture locating device of claim 1, wherein the elongated dilator is elongate along the central axis, wherein the outer surface of defines an outer cross-sectional dimension that is substantially perpendicular to the central axis, wherein the outer cross-sectional dimension is at least 2.60 mm.

6. The puncture locating device of claim 5, wherein the outer cross-sectional dimension is between about 2.60 mm and 5.00 mm.

7. The puncture locating device of claim 1, wherein the flexible barrier is part of a flexible container that is attached to the elongated dilator.

8. The puncture locating device of claim 1, further comprising a handle member disposed on the elongated dilator, wherein the elongated dilator includes a port disposed in the outlet opening, wherein the flexible barrier is attached to the handle member such that the port extends from the elongated dilator to the flexible barrier.

9. A puncture locating device for locating a puncture in a blood vessel, the puncture locating device comprising:
    an elongated dilator having a distal end, a proximal end that is opposite the distal end, an outer surface, an internal channel that extends from the distal end to the proximal end, an inlet opening that is open to the internal channel and is spaced from the distal end, an outlet opening disposed between the proximal end and the inlet opening; and
    a blood pulsation indicator overlying the outlet opening so that the blood pulsation indicator and the outer surface proximate the outlet opening at least partially define and contain an internal volume, wherein the blood pulsation indicator is movably responsive to pulsatile blood flow, such that
    when the elongated dilator is inserted into the puncture of the blood vessel, blood flows into the inlet opening through the outlet opening into the internal volume to cause the blood pulsation indicator to pulse, thereby generating a visual and tactile indication of presence of the inlet opening in the blood vessel.

10. The puncture locating device of claim 9, wherein the blood pulsation indicator includes a flexible barrier.

11. The puncture locating device of claim 10, wherein the flexible barrier is a polymeric material.

12. The puncture locating device of claim 10, wherein the flexible barrier is part of a flexible container that is attached to the elongated dilator.

13. The puncture locating device of claim 10, further comprising a handle member disposed on the elongated dilator, wherein the elongated dilator includes a port disposed in the outlet opening, wherein the flexible barrier is attached to the handle member such that the port extends from the elongated dilator to the flexible barrier.

14. The puncture locating device of claim 9, wherein the elongated dilator includes a plurality of markings disposed along the outer surface between the inlet opening and the outlet opening.

15. The puncture locating device of claim 9, wherein the distal end of the elongated dilator is tapered.

16. The puncture locating device of claim 9, wherein the elongated dilator is elongate along a central longitudinal axis, wherein the outer surface of defines an outer cross-sectional dimension that is substantially perpendicular to the central longitudinal axis, wherein the outer cross-sectional dimension is at least 2.50 mm.

17. The puncture locating device of claim 16, wherein the outer cross-sectional dimension is between about 2.50 mm and 5.00 mm.

\* \* \* \* \*

UNITED STATES PATENT AND TRADEMARK OFFICE
CERTIFICATE OF CORRECTION

| | |
|---|---|
| PATENT NO. | : 11,350,919 B2 |
| APPLICATION NO. | : 16/279577 |
| DATED | : June 7, 2022 |
| INVENTOR(S) | : Walters et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 276 days.

Signed and Sealed this
Tenth Day of June, 2025

Coke Morgan Stewart
*Acting Director of the United States Patent and Trademark Office*